United States Patent
Chiyomaru et al.

[11] 3,937,840
[45] Feb. 10, 1976

[54] COMPOSITIONS AND METHODS OF COMBATTING BACTERIA AND FUNGI USING 2-METHYLBENZANILIDE DERIVATIVES

[75] Inventors: Isao Chiyomaru, Shimizu; Seigo Kawada, Fujieda; Kiyoshi Takita, Shimizu, all of Japan

[73] Assignee: Kumiai Chemical Industry Co., Ltd., Tokyo, Japan

[22] Filed: July 17, 1974

[21] Appl. No.: 489,412

[30] Foreign Application Priority Data
Aug. 18, 1973  Japan.................................. 48-92702

[52] U.S. Cl. ............................................. 424/324
[51] Int. Cl.² ...................... A01N 9/20; A01N 9/24
[58] Field of Search................. 424/324; 260/559 R

[56] References Cited
FOREIGN PATENTS OR APPLICATIONS
1,217,868  12/1970  United Kingdom
1,907,436  2/1969  Germany Primary Examiner—Jerome D. Goldberg
Assistant Examiner—Allen J. Robinson
Attorney, Agent, or Firm—Oblon, Fisher, Spivak, McCleeland & Maier

[57] ABSTRACT

An agricultural germicide having the formula

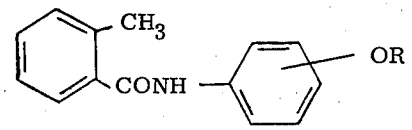

wherein R represents $C_{1-12}$ alkyl, alkenyl, alkynyl, benzyl or chlorobenzyl.

6 Claims, No Drawings

COMPOSITIONS AND METHODS OF COMBATTING BACTERIA AND FUNGI USING 2-METHYLBENZANILIDE DERIVATIVES

BACKGROUND OF THE INVENTION

1. Field of the Invention

This invention relates to an agricultural germicide having the formula

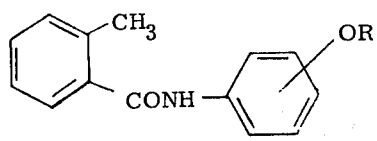

wherein R represents $C_{1-12}$ alkyl, alkenyl, alkynyl, benzyl or chlorobenzyl.

2. Description of the Prior Art

Agricultural germicidal compositions of the o-methylbenzanilide type are effective in preventing diseases, such as rice sheath blight, bacterial leaf blight, tomato late blight, cucumber anthracnose, haricot stem rot, alternaria leaf spot, powdery apple mildew, orange phoma rot, wheat bund, rusting of wheat, barley, turf, coffee, ornamental plants, vegetables, cereals and grasses, smut and Rhizoctonia and Fusarium soil diseases; and are also effective as disinfectants for seeds.

Effective benzanilide compounds are disclosed in German Patent Application Publication No. 1,907,436 and British Pat. No. 1,217,868.

In the former specification, o-methylbenzanilides are disclosed and in the latter specification, benzanilides having the formula

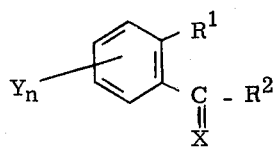

wherein $Y_n$ represents a hydrogen atom, X represents an oxygen atom, $R^2$ represents $NR^3R^4$ wherein $R^3$ represents a hydrogen atom and $R^4$ represents an alkoxyphenyl group, are disclosed.

The prior art compounds are ineffective against certain plant and soil diseases. However, a need continues to exist for agricultural germicides with improved effectiveness for inhibiting plant and soil diseases and improved antimicrobial spectrum.

SUMMARY OF THE INVENTION

Accordingly, one object of the invention is to provide an agricultural germicide with improved effectiveness against plant and soil diseases.

Briefly, this object and other objects of the present invention as hereinafter will become more readily apparent can be attained by agricultural germicide compounds having the formula

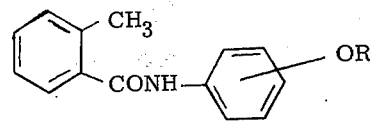

wherein R represents $C_{1-12}$ alkyl, alkenyl, alkynyl, benzyl or chlorobenzyl.

BRIEF DESCRIPTION OF THE PREFERRED EMBODIMENT

Among the o-methylcarboxyanilides of the present invention, 3'-alkoxy-2-methylbenzanilides exhibit especially superior germicidal effects as well as protective and therapeutic effects for sheath blight in rice. The compounds of the invention are permeable in plants so that the compounds may be applied not only by spraying or sprinkling, but also by applying to paddy fields or treating soil. Moreover, the germicidal effect is persistent for a long period of time. The compounds are only slightly toxic to warm blooded animals, so that no noticeable toxic symptoms were observed after oral administration of 10,000 mg/kg to mice.

The compounds of the invention may be prepared by either of the following reactions.

Reaction (I)

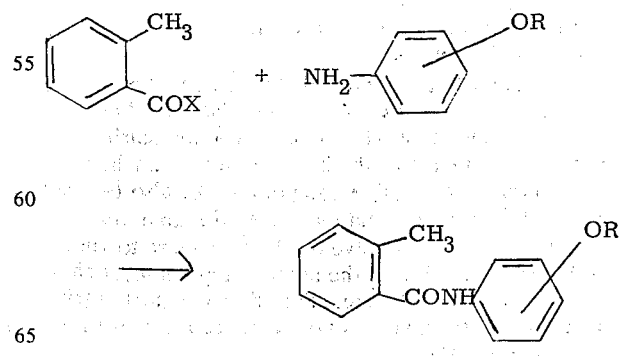

Reaction (II)

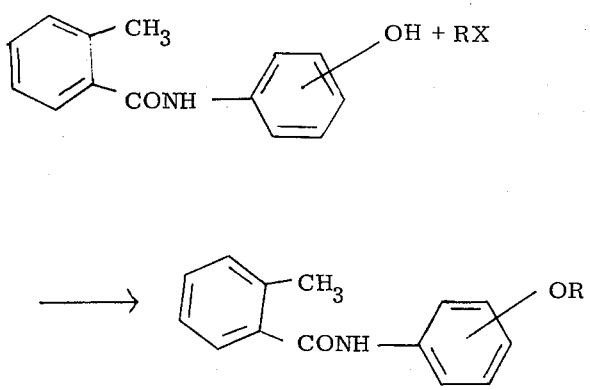

Reaction (III)

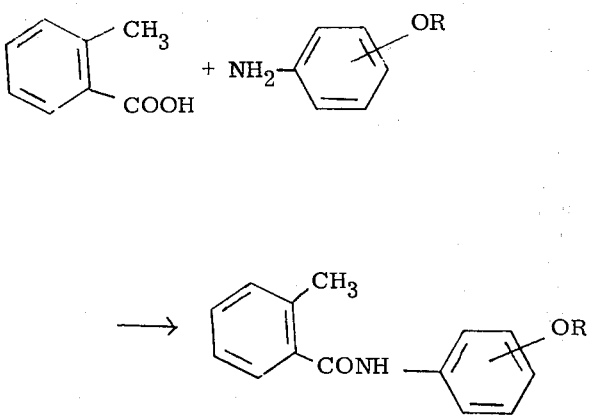

In the reactions, X represents a halogen (Cl, Br, I) and R is defined as above.

In Reaction (I), suitable dehydrohalogenating agents include tertiary amines, e.g., triethylamine, dimethylaniline, pyridine; or alkalis, e.g., sodium carbonate, sodium bicarbonate or the like. Twice the stoichiometric amount of the aniline compound may also be used as the dehydrohalogenating agent. Suitable reaction solvents include any solvent which is inert to the o-methylbenzoylhalide or the aniline compound, such as benzene, toluene, acetone, ether, dioxane, acetonitrile, or the like. A suitable reaction temperature is between −20° to about 100°C.

In reaction (II), suitable dehydrohalogenating agents include tertiary amines and alkali carbonates or hydroxides, e.g., sodium hydroxide, potassium hydroxide, or the like. Suitable reaction solvents include the solvents used in reaction (I) as well as water and lower aliphatic alcohols. A suitable reaction temperature is between −20° and about 100°C, which will produce a high yield.

In reaction (III), the compounds may be prepared by the addition of a dehydrating agent to a mixture of o-toluic acid and the aniline compound, in the presence or absence of a base, by a one step reaction. Reaction (III) is the most advantageous industrially for obtaining high purity compounds in high yields. In reaction (III), suitable dehydrating agents include phosphorus oxychloride, phosphorus trichloride, phosphorous pentachloride, phosphorus tribromide, thionyl chloride, sulfuryl chloride, sulfonic acids, sulfuric acid, hydrogen halides, carbodiimides, alumina and silica. Suitable bases include tertiary amines, e.g., trimethyl amine and pyridine; carbonates, e.g., sodium carbonate and sodium bicarbonate; and alkali hydroxides, e.g., sodium hydroxide. Suitable reaction solvents include benzene, toluene, xylene, chlorobenzene, acetone, methylethylketone, ether, dioxane, tetrahydrofuran, dimethyl formamide, acetonitrile, chloroform, carbon tetrachloride or the like. A suitable reaction temperature is between −20° and about 200°C, and a suitable reaction time is 1 - 20 hours.

Having generally described this invention, a further understanding can be obtained by reference to certain specific examples which are provided herein for purposes of illustration only and are not intended to be limiting unless otherwise specified.

EXAMPLE 1

Preparation of 3'-methoxy-2-methylbenzamide

A 15.5 g (0.1 mol) portion of o-methylbenzoyl chloride was added dropwise to a stirred solution of 11.9 g (0.1 mol) of m-methoxyaniline and 10.1 g (0.1 mol) of triethylamine in 250 ml of ether and the resulting solution was cooled. After addition of the o-methylbenzoylchloride, the mixture was stirred at room temperature for an additional 5 hours, and the reaction mixture was washed with water to remove triethylamine hydrochloride. The ether layer was dried over anhydrous sodium sulfate and the ether was removed whereby 23.9 g (99%) of fine white prisms having a melting point of 142°–143°C were obtained. IR cm$^{-1}$ (KBr-tablet), $\nu_{NH}$3250 (S). $\nu_{CO}$1655(S), 1610(S).

EXAMPLE 2

Preparation of 2'-ethoxy-2-methylbenzanilide

A 19.9 g (0.1 mol) portion of o-methylbenzoyl bromide was added dropwise with cooling to a mixture of 13.7 g (0.1 mol) of o-ethoxyaniline and 8.4 g (0.1 mol) of sodium bicarbonate in 200 ml of acetone with stirring. After addition of the o-methylbenzoyl bromide, the reaction mixture was warmed to 40°C and the mixture was refluxed and stirred for another 40 hours. After filtering, the ether was distilled from the reaction mixture and the residual material was re-dissolved in ether and washed with water. The ether layer was dried over anhydrous sodium sulfate, the ether was removed and the product was distilled to obtain 24.1 g (94.5%) of a clear pink liquid having a boiling point of 148°C/0.04 mm Hg and $n_D^{20}$ of 1.5929. IR cm$^{-1}$ (film) $\nu_{NH}$3295(S), $\nu_{CO}$ 1655,1615(S).

EXAMPLE 3

Preparation of 3'-iso-propoxy-2-methylbenzanilide

A 22.7 g (0.1 mol) portion of 3'-hydroxy-2-methylbenzanilide was dissolved in 100 ml of 1N-potassium hydroxide solution. To this solution 150 ml of ethanol was added and the mixture was stirred for one hour, which was followed by the addition of 12.3 g (0.1 mol) of isopropylbromide. After the addition of the isopropylbromide, the reaction mixture was warmed and stirred under reflux for 4 hours. After distillation of most of the ethanol, the oily material remaining was extracted with benzene and the residue was distilled to obtain 20.9 g (77.9%) of a red, viscous oil having a boiling point of 186°C/0.08 mm Hg. The product was recrystallized from a mixture of benzene and n-hexane (1:1) as white prismatic crystals having a melting point of 92°C. IR cm$^{-1}$ (KBr-tablet) $\nu_{NH}$ 3250(S), $\nu_{CH}$ 2980(S), $\nu_{CO}$ 1660(S), 1610(S).

EXAMPLE 4

Preparation of 3'-n-butoxy-2-methylbenzanilide

A 22.7 g (0.1 mol) portion of 3'-hydroxy-2-methylbenzanilide was dissolved in 80 ml of dimethyl sulfoxide and to this solution was added a solution of 5.6 g (0.1 mol) of potassium hydroxide in 40 ml of water. The white mixture was cooled with water, and 30 ml of dimethyl sulfoxide containing 13.7 g (0.1 mol) of n-butylbromide was added dropwise to the solution with stirring. After the addition, the mixture was warmed and kept at 40° to 50°C for 3 hours. The reaction mixture was poured into 700 ml of water and the oily material formed was extracted with benzene. The benzene layer was washed with water, dehydrated over anhydrous sodium sulfate and the benzene was removed to obtain the product, which was recrystallized from a mixture of benzene and n-hexane (1:2) to obtain 26.3 g (92.9%) of greyish needle-like crystals having a melting point of 87°C. IR cm$^{-1}$ (KBr-tablet) $\nu_{NH}$ 3260(S), $\nu_{CO}$ 1645(S), 1620(S).

EXAMPLE 5

Preparation of 3'-n-amyloxy-2-methylbenzanilide

A 22.7 g (0.1 mol) portion of 3'-hydroxy-2-methylbenzanilide was dissolved in 80 ml of dimethyl sulfoxide and to this solution was added a solution of 4.0 g (0.1 mol) of sodium hydroxide in 40 ml of water. The whole mixture was cooled with ice water and 15.1 g (0.1 mol) of n-amylbromide was added dropwise with stirring. After the addition, the reaction mixture was warmed and kept at 70° to 80°C for 3 hours. The reaction mixture was poured into 500 ml of water, and the precipitated product was filtered and washed with water and dried. The product was recrystallized from ethanol to obtain 23.8 g (80.0%) of white needles having a melting point of 90°C. IR cm$^{-1}$ (KBr-tablet) $\nu_{NH}$ 3270(S), $\nu_{CO}$ 1645(S).

EXAMPLE 6

Preparation of 3'-allyloxy-2-methylbenzanilide

A 22.7 g (0.21 mol) portion of 3'-hydroxy-2-methylbenzanilide was mixed with 5.6 g of KOH dissolved in 120 ml of ethanol, and the mixture was added with cooling and stirring to 12.1 g (0.1 mol) of allylbromide. After the addition, the reaction mixture was warmed and kept at 40°C to 50°C for 2 hours. The reaction mixture was poured into 500 ml of ice water, and the precipitated product was filtered and washed with water and dried. The product was recrystallized from ethanol to obtain 20.2 g (75.5%) of white powdery crystals having a melting point of 85°–89°C. IR cm$^{-1}$ (KBr-tablet) $\nu_{NH}$3250(S), $\nu_{CO}$1655(S).

EXAMPLE 7

Preparation of 3'-propargyloxy-2-methylbenzanilide

A mixture of 22.7 g (0.1 mol) of 3'-hydroxy-2-methylbenzanilide, 11.9 g (0.1 mol) of propargylbromide, 10.6 g (0.1 mol) of sodium carbonate and 250 ml of acetone was prepared and the mixture was refluxed for 4 hours with stirring. After cooling, the reaction mixture was filtered and the acetone was removed by distillation. The residual material was dissolved in benzene, washed with water and dehydrated over anhydrous sodium sulfate. The benzene was removed and the product was recrystallized from aqueous ethanol to obtain a 23.2 g (87.7%) of fine white needles having a melting point of 93°–95°C.

EXAMPLE 8

Preparation of 3'-benzyloxy-2-methylbenzanilide

A 9.1 g (0.04 mol) portion of 3'-hydroxy-2-methylbenzanilide was dissolved in a solution of 2.3 g (0.041 mol) of potassium hydroxide in 50 ml of ethanol, and 5.1 g (0.04 mol) of benzylchloride was added dropwise to the above solution with stirring at room temperature. After the addition, the reaction mixture was warmed and refluxed for 3 hours. The reaction mixture was poured into 200 ml of water and the precipitated product was filtered and washed with water and dried. The product was recrystallized from 90% methanol to obtain 7.5 g (60.5%) of white needles having a melting point of 114°–115°C. IR cm$^{-1}$ (KBr-tablet) $\nu_{NH}$3230 (m), $\nu_{CO}$1645 (S).

EXAMPLE 9

Preparation of 3'-methoxy-2-methylbenzanilide

A 13.6 g (0.1 mol) portion of o-methylbenzoic acid, 10.9 g (0.1 mol) of m-methoxyaniline and 10.1 g (0.1 mol) of triethylamine were dissolved in 250 ml of toluene. A 4.6 g (0.033 mol) amount of phosphorus trichloride was added dropwise to the above solution with stirring at 20°–60°C. After the addition, the reaction mixture was stirred at 80°–90°C for 3 hours. The reaction mixture was cooled and washed with water to remove the triethylamine hydrochloride, and the product was dried over anhydrous sodium sulfate. The toluene was removed to give 22.8 g (95%) of fine white prismatic crystals having a melting point of 142°–143°C.

EXAMPLE 10

Preparation of 2'-ethoxy-2-methylbenzanilide

A 13.6 g (0.1 mol) portion of o-methylbenzoic acid and 13.7 g of o-ethoxyaniline were dissolved in 200 ml of acetone. A 4.7 g (0.033 mol) amount of phosphorus pentoxide was gradually added to the prepared solution at 30°–40°C. After the addition, the reaction mixture was refluxed for 3 hours with stirring. The acetone was removed and the residual product was poured into water and was extracted with toluene. The toluene layer was dried over anhydrous sodium sulfate and the toluene was removed to obtain 24.1 g (94.5%) of a clear pink liquid, having a boiling point of 148°C/0.04 mm Hg and $n_D^{20}$ of 1.5929.

EXAMPLE 11

Preparation of 3'-iso-propoxy-2-methylbenzanilide

A 13.6 g (0.1 mol) portion of o-methylbenzoic acid, 15.1 g (0.1 mol) of m-isopropoxyaniline and 10.1 g (0.1 mol) of triethylamine were dissolved in 100 ml of xylene. A 5.1 g (0.033 mol) amount of phosphorus oxychloride was added dropwise to the prepared solution with stirring at 90°–100°C. Stirring of the resulting solution was continued at 90°–100°C for 3 hours. The reaction mixture was cooled and washed with water, and the product was dried over anhydrous sodium sulfate. The xylene was removed to obtain 20.9 g (77.9%) of white prismatic crystals having a melting point of 92°–94°C.

EXAMPLE 12

Preparation of 3'-n-propoxy-2-methylbenzanilide

A 13.6 g (0.1 mol) portion of o-methylbenzoic acid and 15.1 g (0.1 mol) of m-n-propoxy-aniline were dissolved in 100 ml of chlorobenzene. An 11.9 g (0.1 mol) amount of thionylchloride was added dropwise to the prepared solution at 40°–50°C, and the mixture was stirred at 90°–95°C for 4 hours, whereby sulfur dioxide and hydrogen chloride were continuously generated. After the reaction, the reaction mixture was poured into ice water and extracted with a mixture of benzene and hexane. The product was recrystallized from the mixed solvent to obtain 23.6 g (88%) of white needles having a melting point of 92°–94°C.

Typical active ingredients prepared by the above processes are listed below. The compound numbers appearing below will be referred to later in the text.

Compound No. 1
2'-methoxy-2-methylbenzanilide
white prisms
melting point 74°–75°C Compound No. 2
3'-methoxy-2-methylbenzanilide
fine white prisms
melting point 142°–143°C Compound No. 3
4'-methoxy-2-methylbenzanilide
white needles
melting point 136°–137°C Compound No. 4
2'-ethoxy-2-methylbenzanilide
clear pinkish oil
boiling point 148°C/0.04 mm Hg Compound No. 5
3'-ethoxy-2-methylbenzanilide
white needles
melting point 115°–116°C Compound No. 6
4'-ethoxy-2-methylbenzanilide
white needles
melting point 149°–149.5°C Compound No. 7
2'-iso-propoxy-2-methylbenzanilide
clear reddish brown oil
boiling point 143°–145°C/0.01 mm Hg Compound No. 8
3'-iso-propoxy-2-methylbenzanilide
white prisms
melting point 92°C Compound No. 9
4'-n-propoxy-2-methylbenzanilide
powdery white crystals
melting point 151°–152°C Compound No. 10
3'-n-pentyloxy-2-methylbenzanilide
white needles
melting point 90°C Compound No. 11
3'-octyloxy-2-methylbenzanilide
white needles
melting point 95°C Compound No. 12
3'-n-dodecyloxy-2-methylbenzanilide
powdery white crystals
melting point 65°–66°C Compound No. 13
2'-allyloxy-2-methylbenzanilide
pale reddish brown oil
boiling point 151°C/b 0.025 mm Hg Compound No. 14
3'-allyloxy-2-methylbenzanilide
powdery white crystals
melting point 85°–89°C Compound No. 15
3'-propargyloxy-2-methylbenzanilide
fine white powder
melting point 93°–95°C Compound No. 16
3'-benzyloxy-2-methylbenzanilide
white needles
melting point 114°–115°C Compound No. 17
3'-2-chlorobenzyloxy-2-methylbenzanilide
fine white needles
melting point 116°C Compound No. 18
3'-n-propoxy-2-methylbenzanilide
white prisms
melting point 92°–93°C Compound No. 19
2'-sec-butoxy-2-methylbenzanilide
white needles
melting point 75°–77°C Compound No. 20
3'-n-butoxy-2-methylbenzanilide
greyish needles
melting point 87°C The active ingredients may be used in the form of conventional compositions, e.g., solutions, emulsions, wettable powders, fine granules, granules, and dust. However, the active ingredient alone may be applied. These compositions may be prepared by conventionally mixing the active ingredient with a diluting agent, such as a liquid or solid carrier, and if necessary, with an emulsifier or a dispersing agent. Suitable liquid diluents or carriers include water, aromatic hydrocarbons, e.g., xylene, benzene and methyl naphthalene; chlorinated aromatic hydrocarbons, e.g., chlorobenzene; mineral oils, e.g., paraffin; alcohols, e.g., methanol, propanol; polar solvents, e.g., dimethylformamide, dimethylsulfoxide, or the like. Suitable solid diluents or carriers include talc, clay, kaolin, hydrated silica, wood powder, sand, or the like. Suitable emulsifiers include polyoxyethylene esters of aliphatic carboxylic acids, polyoxyethylene ethers of aliphatic alcohol or the like. Suitable dispersing agents include alkali metal salts, alkaline earth metal salts or ammonium salts of alkyl sulfonic acids, alkylarylsulfonic acids or lignin sulfonic acids, and methylcellulose or the like.

Synergistic effects may be obtained when the active ingredient is combined with other germicidal compounds, e.g., Neo-Asozin(ferric ammonium salts of methane arsonic acid), Polyoxin (antibiotic fungicide), Validamycin (antibiotic fungicide), Phenazin (phenazin-5-oxide); insecticidal compounds, e.g., Sumithion (O,O-dimethyl) O-(3-methyl-4-nitrophenyl)phosphorothioate), Baycid (O,O-dimethyl O-(3-methyl-4-methylthiophenyl)phosphorothioate) or spanon (hydrochloric acid salt of N-(2-methyl-4-chlorophenyl)-N,N-dimethylformamidine). The active ingredients may also be combined with fertilizers, soil conditions, or the like. The compounds of the invention are preferably applied in the following quantities.

Dilute solution:
 50–300 l of 100–2,000 ppm dilution per 10 a
Powder composition:
 1–5 Kg of 0.5–10% powder formulation per 10 a.
Soil treatment:
 100–5,000 g of the active ingredient per 10 a.
Seed treatment:
 A seed is coated with 0.01–5% of the active ingredient based on the weight of the seed.
Typical compositions are listed below.
Composition No. 1 — Powder Compound No. 1 (4%), diatomaceous earth (5%) and clay (91%) were crushed and mixed uniformly to give a dust formulation.

Composition No. 2 — Wettable Powder

Compound No. 2 (50%) diatomaceous earth (45%), sodium dinaphthylmethane sulfonate (2%) and sodium lignin sulfonate (3%) were mixed and uniformly crushed to give a wettable powder.

Composition No. 3 — Emulsion

Compound No. 3 (30%), cyclohexanone (20%), polyoxyethylene alkylaryl ether (11%), calcium alkylbenzene sulfonate (4%) and methyl naphthalene (35%) were uniformly mixed to give an emulsifiable concentrate.

Composition No. 4 — Fine granules

To 4% polyethylene glycol was added 60°–250 mesh sea sand and the mixture was thoroughly stirred to coat the polyethyleneglycol uniformly onto the sand. The mixture prepared above (94%), and 6% of a mixture composed of 70% Compound 5 and 30% clay were thorougly stirred to give the granules.

Composition No. 5 — Granules

Compound No. 5 (10%), sodium lauryl sulfate (2%), sodium lignin sulfonate (5%), carboxymethyl cellulose (2%) and clay (81%) were mixed uniformly and crushed. Water (20%) was added to the mixture, which was kneaded and extruded with an extrusion granulating machine. The mixture was dried and granulated using 14–32 mesh sieves to obtain granules.

The agricultural effects of the compounds of the invention are shown in the experiments below.

EXPERIMENT 1

Protective effect against rice sheath blight

Fifteen young rice plants (Oryza sativa L.var Kinmaze) were transplanted to a pot with contents resembling paddy-field conditions, and, at the six-leaf stage, the plants were sprayed with the germicidal wettable powder, "Composition No. 2", suspended in water. After drying, a portion of 3-day-old cultures of Pellicuralia sasakii, grown on potato sucrose agar medium in Petri dishes at 28°C, was picked and inoculated into the leaf sheath of the plants, which were then left for 8 days in a high humidity chamber kept at 28°C. The length of the infection or infestation lesion formed on the sheath of the rice plant was measured. The results of the tests (3 pots were used for each test) are shown in Table 1.

The protection value was calculated as follows:

$$\text{Protection value (\%)} = \left[ 1 - \frac{\text{total length of lesions in treated plants}}{\text{total length of lesions in non-treated plants}} \right] \times 100$$

TABLE 1

| Germicidal ingredient | Concentration (ppm) | Total length of lesions (cm) | Protection value (%) | (Chemical injury) phytotoxicity |
| --- | --- | --- | --- | --- |
| Compound No. 1 | 500 | 14.2 | 95.5 | None |
| No. 2 | " | 4.5 | 98.6 | " |
| No. 3 | " | 32.5 | 89.6 | " |
| No. 4 | " | 4.3 | 98.6 | " |
| No. 5 | " | 0 | 100 | " |
| No. 6 | " | 42.5 | 86.4 | " |
| No. 7 | " | 1.4 | 99.6 | " |
| No. 8 | " | 0 | 100 | " |
| No. 9 | " | 24.5 | 92.1 | " |
| No. 10 | " | 4.5 | 98.6 | " |
| No. 11 | " | 14.3 | 95.5 | " |
| No. 12 | " | 42.5 | 86.4 | " |
| No. 13 | " | 3.2 | 99.0 | " |
| No. 14 | " | 0 | 100 | " |
| No. 15 | " | 0 | 100 | " |
| No. 16 | " | 0 | 100 | " |

Table 1-continued

| Germicidal ingredient | | Concentration (ppm) | Total length of lesions (cm) | Protection value (%) | (Chemical injury) phytotoxicity |
|---|---|---|---|---|---|
| | No. 17 | '' | 12.5 | 96.0 | '' |
| | No. 18 | '' | 0 | 100 | '' |
| | No. 19 | '' | 0 | 100 | '' |
| | No. 20 | '' | 4.3 | 98.6 | '' |
| *Reference Compound | No. 101 | 500 | 228.4 | 26.8 | None |
| | 102 | '' | 253.2 | 18.9 | '' |
| | 103 | '' | 269.3 | 13.7 | '' |
| | 104 | '' | 310.4 | 0.5 | '' |
| | 105 | '' | 292.5 | 6.3 | '' |
| | 106 | '' | 310.6 | 0.5 | '' |
| | 107 | '' | 194.5 | 37.7 | '' |
| Polyoxine PS emulsion | | 25 | 43.2 | 86.2 | None |
| Neo-Asozine solution | | 16.2 | 0 | 100 | '' |
| Non-treated | | — | 312.1 | 0 | '' |

Polyoxine PS emulsion — Antibiotic Fungicide, Active Ingredient as polyoxin B. . .3% 30,000 Dmu/g Neo-Asozine solution — Ferric ammonium salts of methane arsonic acid, active ingredient. . .6.5%

The reference compounds are disclosed in German Application No. 1,907,436 and British patent No. 1,217,868.

*Reference compound
No. 101 2-methylbenzanilide
No. 102 2'-methyl-2-methylbenzanilide
No. 103 2'-ethyl-2-methylbenzanilide
No. 104 4'-ethyl-2-methylbenzanilide
No. 105 4'-hydroxy-2-methylbenzanilide
No. 106 4'-methoxy-2-chlorobenzanilide
No. 107 4'-methoxy-2-nitrobenzanilide

EXPERIMENT 2

Therapeutic effect on rice plant sheaths

Fifteen rice plant seedlings (Oryza sativa L.var Kinmaze) were transplanted to a pot duplicating paddy-field conditions. A portion of 2-day-old cultures (Pellicuralia sasakii), grown on potato sucrose agar medium in Petri dishes at 28°C, was inoculated into the sheaths of the seedlings, which were then kept for 2 days in a high humidity chamber at 28°C. Then seedlings were sprayed with the suspension of a wettable powder, Composition No. 2, in water. The sprayed seedlings were kept for another 6 days in the above chamber. The lengths of lesions formed on the sheaths of the plants were measured. The results of the tests (3 pots were used for each test) are shown in Table 2. The therapeutic value was calculated as follows:

EXPERIMENT 3

Protective effect against Sheath blight in rice plants

Fifteen rice plants at the six-leaf stage (Oryza sativa L.var Kinmaze) were planted in a pot having a diameter of 15 cm, and 10% granules of the compounds shown in the following Table 3, which were prepared similarly to "Composition No. 5", were uniformly delivered to the surface water of the pot in a given dosage. The plants were then kept in a greenhouse. Seven days after the treatment, 3-day-old cultures (Pellicuralia sasakii), grown on a potato sucrose agar medium in Petri-dishes at 28°C, were inoculated into the sheath of the seedlings, which were then left for 8 days in a high humidity chamber at 28°C. The lengths of the infested lesions formed on the sheaths of the rice plants were measured. The results of the tests (3 pots were used for each test) are shown in Table 3. The protection value was calculated as follows:

$$\text{Therapeutic value (\%)} = 1 - \left[\frac{\text{Total length of lesions in treated plants}}{\text{Total length of lesions in non-treated plants}}\right] \times 100$$

TABLE 2

| Germicidal ingredient | | Total length of lesions (cm) | | Therapeutic value (%) | | Phytotoxicity (Chemical injury) | |
|---|---|---|---|---|---|---|---|
| | | CONCENTRATION | | | | | |
| | | 500 ppm | 50 ppm | 500 ppm | 50 ppm | 500 ppm | 50 ppm |
| Compound | No. 1 | 29.2 | [229.5] | 91.1 | [26.3] | None | [None] |
| | No. 2 | 0 | [7.2] | 100 | [97.7] | '' | ['''] |
| | No. 3 | 42.5 | [284.5] | 87.0 | [8.6] | '' | ['''] |
| | No. 4 | 8.4 | [240.3] | 97.4 | [22.8] | '' | ['''] |
| | No. 5 | 0 | [0] | 100 | [100] | '' | ['''] |
| | No. 6 | 38.4 | [259.0] | 88.2 | [16.8] | '' | ['''] |
| | No. 7 | 10.3 | [236.2] | 96.8 | [24.1] | '' | ['''] |
| | No. 8 | 0 | [0] | 100 | [100] | '' | ['''] |
| | No. 9 | 24.5 | [294.5] | 92.5 | [5.4] | '' | ['''] |
| | No. 10 | 0 | [13.4] | 100 | [95.7] | '' | ['''] |
| | No. 14 | 0 | [12.4] | 100 | [96.0] | '' | ['''] |
| | No. 15 | 0 | [10.7] | 100 | [96.6] | '' | ['''] |
| | No. 18 | 0 | [0] | 100 | [100] | '' | ['''] |
| | No. 19 | 0 | [0] | 100 | [100] | '' | ['''] |
| | No. 20 | 0 | [0] | 100 | [100] | '' | ['''] |
| Non-treated | | 326.4 | [311.2] | 0 | [0] | '' | ['''] |

Protection value (%) = $\left[1 - \dfrac{\text{total length of lesions in treated plants}}{\text{total length of lesions in non-treated plants}}\right] \times 100$

TABLE 3

| Germicidal ingredient | | Protection value (%) Dosage in active ingredient (500 g/10 a) | (Chemical injury) Phytotoxicity |
| --- | --- | --- | --- |
| Compound | No. 2 | 97.5 | None |
| | No. 5 | 100 | None |
| | No. 8 | 100 | None |
| | No. 10 | 94.9 | None |
| | No. 14 | 96.2 | None |
| | No. 15 | 95.7 | None |
| | No. 18 | 98.3 | None |
| | No. 19 | 100 | None |
| | No. 20 | 96.2 | None |
| Non-treated | | 0 | None |

EXPERIMENT 4

Effect on cotton seedling blight

The cotton seeds were treated with wettable powders prepared following the procedure described in Composition No. 2 in amounts of 1.0, 0.5 or 0.1% by weight of the cotton seeds. Rhizoctonia solani, cultured on wheat bran culture and diluted 40 times with soil, was used to fill each pot having a diameter of 15 cm, and 20 of the treated cotton seeds were sown in the soil. The pots were kept in a greenhouse until the seedlings grew to the two-leaf stage and were then kept in an inoculation chamber at 25°C at a relative humidity of 90% for 2 days. The number of normally grown seedlings was counted. Three pots were used for each treatment.

Percent normally grown seedling = $\dfrac{\text{Number of normally grown seedlings}}{\text{Total number of seedlings}} \times 100$

TABLE 4

| Germicidal ingredient | Concentration (%) | Percent normally grown seedling | (Chemical injury) Phytotoxicity |
| --- | --- | --- | --- |
| Compound No. 1 | 1.0 | 100 | None |
| | 0.5 | 95.0 | None |
| | 0.1 | 80.0 | None |
| Compound No. 2 | 1.0 | 100 | None |
| | 0.5 | 100 | None |
| | 0.1 | 100 | None |
| Compound No. 3 | 1.0 | 100 | None |
| | 0.5 | 92.5 | None |
| | 0.1 | 77.5 | None |
| Compound No. 4 | 1.0 | 100 | None |
| | 0.5 | 100 | None |
| | 0.1 | 97.5 | None |
| Compound No. 5 | 1.0 | 100 | None |
| | 0.5 | 100 | None |
| | 0.1 | 100 | None |
| Compound No. 6 | 1.0 | 100 | None |
| | 0.5 | 92.5 | None |
| | 0.1 | 85.0 | None |
| Compound No. 7 | 1.0 | 100 | None |
| | 0.5 | 100 | None |
| | 0.1 | 100 | None |
| Compound No. 8 | 1.0 | 100 | None |
| | 0.5 | 100 | None |
| | 0.1 | 100 | NOne |
| Compound No. 9 | 1.0 | 100 | None |
| | 0.5 | 100 | None |
| | 0.1 | 90.0 | None |
| Compound No. 13 | 1.0 | 100 | None |
| | 0.5 | 100 | None |
| | 0.1 | 100 | None |
| Compound No. 14 | 1.0 | 100 | None |
| | 0.5 | 100 | None |
| | 0.1 | 100 | None |
| Compound No. 15 | 1.0 | 100 | None |
| | 0.5 | 100 | None |
| | 0.1 | 100 | None |
| Compound No. 16 | 1.0 | 100 | None |
| | 0.5 | 100 | None |
| | 0.1 | 100 | None |
| Compound No. 17 | 1.0 | 100 | None |
| | 0.5 | 95.0 | None |
| | 0.1 | 80.0 | None |
| Benlate 50% wettable powder | 1.0 | 95.0 | None |
| | 0.5 | 72.5 | None |
| | 0.1 | 45.0 | None |
| Non-treated | | 0 | None |

Benlate = [(1-butylcarbamoyl)-2-benzimidazol carbamic acid methyl ester]

EXPERIMENT 5

Effect on Bakanae disease in rice plants

Wettable powders prepared similarly to Composition No. 2 were applied to rice seeds which were naturally infected with Gibberella fujikuroi in amounts of 0.2%, 0.1%, or 0.05% by weight of the rice seeds. Rice seeds (100) were sown into pots filled with soil, were kept at 30°–35°C at a relative humidity of 90% for 10 days and then were kept in a greenhouse at high humidity for 15 days. The number of infected seedlings was counted.

infected seedlings (%) = $\dfrac{\text{number of infected seedlings}}{\text{total number of seeding}} \times 100$

TABLE 5

| Germicidal ingredient | Concentration (%) | Infected Seedling (%) | Phytotoxicity |
| --- | --- | --- | --- |
| Compound No. 1 | 0.2 | 0 | None |
| | 0.1 | 3 | None |
| | 0.05 | 12 | None |
| Compound No. 2 | 0.2 | 0 | None |
| | 0.1 | 0 | None |
| | 0.05 | 0 | None |
| Compound No. 3 | 0.2 | 0 | None |
| | 0.1 | 4 | None |
| | 0.05 | 16 | None |
| Compound No. 4 | 0.2 | 0 | None |
| | 0.1 | 0 | None |
| | 0.05 | 7 | None |
| Compound No. 5 | 0.2 | 0 | None |
| | 0.1 | 0 | None |
| | 0.05 | 0 | None |
| Compound No. 6 | 0.2 | 0 | None |
| | 0.1 | 0 | None |
| | 0.05 | 4 | None |
| Compound No. 7 | 0.2 | 0 | None |
| | 0.1 | 0 | None |
| | 0.05 | 0 | None |
| Compound No. 8 | 0.2 | 0 | None |
| | 0.1 | 0 | None |
| | 0.05 | 0 | None |
| Compound No. 9 | 0.2 | 0 | None |
| | 0.1 | 4 | None |
| | 0.05 | 12 | None |
| Compound No. 13 | 0.2 | 0 | None |
| | 0.1 | 0 | None |
| | 0.05 | 2 | None |

$$\text{infected seedlings (\%)} = \frac{\text{number of infected seedlings}}{\text{total number of seeding}} \times 100$$

TABLE 5

| Germicidal ingredient | Concentration (%) | Infected Seedling (%) | Phytotoxicity |
|---|---|---|---|
| Compound No. 14 | 0.2 | 0 | None |
|  | 0.1 | 0 | None |
|  | 0.05 | 0 | None |
| Compound No. 15 | 0.2 | 0 | None |
|  | 0.1 | 0 | None |
|  | 0.05 | 0 | None |
| Compound No. 16 | 0.2 | 0 | None |
|  | 0.1 | 0 | None |
|  | 0.05 | 0 | None |
| Compound No. 17 | 0.2 | 0 | None |
|  | 0.1 | 2 | None |
|  | 0.05 | 8 | None |
| *Reference Compound No. 101 | 0.2 | 3 | None |
|  | 0.1 | 19 | None |
|  | 0.05 | 42 | None |
| Reference Compound No. 102 | 0.2 | 6 | None |
|  | 0.1 | 16 | None |
|  | 0.05 | 38 | None |
| Reference Compound No. 103 | 0.2 | 8 | None |
|  | 0.1 | 21 | None |
|  | 0.05 | 42 | None |
| Reference Compound No. 104 | 0.2 | 10 | None |
|  | 0.1 | 25 | None |
|  | 0.05 | 47 | None |
| Reference Compound No. 105 | 0.2 | 13 | None |
|  | 0.1 | 26 | None |
|  | 0.05 | 51 | None |
| Reference Compound No. 106 | 0.2 | 9 | None |
|  | 0.1 | 17 | None |
|  | 0.05 | 36 | None |
| Reference Compound No. 107 | 0.2 | 12 | None |
|  | 0.1 | 22 | None |
|  | 0.05 | 48 | None |
| Benlate 50% wettable powder | 0.2 | 9 | None |
|  | 0.1 | 14 | None |
|  | 0.05 | 34 | None |
| Non-treated | — | 65 | None |

The reference compounds are disclosed in German Application No. 1,907,436 and British Patent No. 1,217,868.
*Reference compound
No. 101 2-methylbenzanilide
No. 102 2'-methyl-2-methylbenzanilide
No. 103 2'-ethyl-2-methylbenzanilide
No. 104 4'-ethyl-2-methylbenzanilide
No. 105 4'-hydroxy-2-methylbenzanilide
No. 106 4'-methoxy-2-chlorobenzanilide
No. 107 4'-methoxy-2-nitrobenzanilide

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method of protecting plants against agricultural fungi or bacteria, which comprises: applying a fungicidally or bactericidally effective amount of a 2-methylbenzanilide compound having the formula

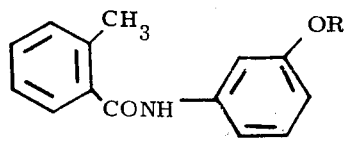

wherein R represents $C_{1-12}$ alkyl, to plants, seeds or soil.

2. A method of protecting plants against agricultural fungi or bacteria, which comprises: applying a fungicidally or bactericidally effective amount of a 2-methylbenzanilide compound having the formula

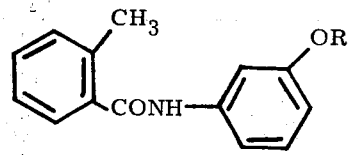

wherein R represents allyl to plants, seeds or soil.

3. A method of protecting plants against agricultural fungi or bacteria, which comprises: applying a fungicidally or bactericidally effective amount of a 2-methylbenzanilide compound having the formula

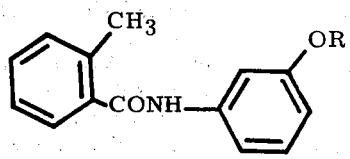

wherein R represents propargyl to plants, seeds or soil.

4. Fungicidal or bactericidal composition which comprises an inert carrier and as an active ingredient, a fungicidally or bactericidally effective amount of a 2-methylbenzanilide compound having the formula

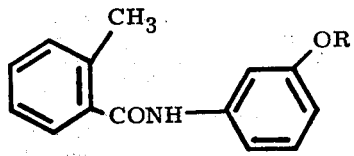

wherein R represents $C_{1-12}$ alkyl.

5. Fungicidical or bactericidal composition which comprises an inert carrier and as an active ingredient, a fungicidally or bactericidally effective amount of a 2-methylbenzanilide compound having the formula

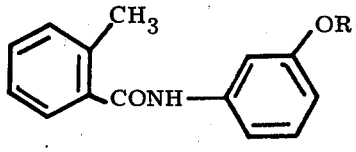

wherein R represents allyl.

6. Fungicidal or bactericidal composition which comprises an inert carrier and as an active ingredient, a fungicidally or bactericidally effective amount of a 2-methylbenzanilide compound having the formula

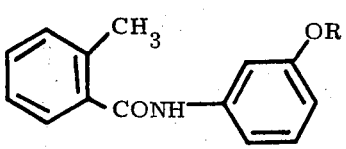

wherein R represents propargyl.

* * * * *